US012102094B2

(12) United States Patent
Ursella et al.

(10) Patent No.: US 12,102,094 B2
(45) Date of Patent: Oct. 1, 2024

(54) METHOD AND PLANT FOR INSPECTING AN ANIMAL CARCASS

(71) Applicant: BIOMETIC S.R.L., Bressanone (IT)

(72) Inventors: Enrico Ursella, Mestre (IT); Giancarlo Zane, Mestre (IT); Arianna Giudiceandrea, Bressanone (IT)

(73) Assignee: BIOMETIC S.R.L., Bressanone (IT)

( * ) Notice: Subject to any disclaimer, the term of this patent is extended or adjusted under 35 U.S.C. 154(b) by 14 days.

(21) Appl. No.: 18/079,992

(22) Filed: Dec. 13, 2022

(65) Prior Publication Data

US 2023/0180770 A1 Jun. 15, 2023

(30) Foreign Application Priority Data

Dec. 15, 2021 (IT) .................. 102021000031448

(51) Int. Cl.
*A22B 5/00* (2006.01)
*G01N 23/083* (2018.01)

(52) U.S. Cl.
CPC .......... *A22B 5/0041* (2013.01); *G01N 23/083* (2013.01); *G01N 2223/419* (2013.01)

(58) Field of Classification Search
CPC ... A22B 5/0041; A22B 5/0007; A22B 5/0064; G01N 23/083
USPC ........................................................ 452/149
See application file for complete search history.

(56) References Cited

U.S. PATENT DOCUMENTS

| | | | | |
|---|---|---|---|---|
| 5,162,016 A | * | 11/1992 | Malloy | A22B 5/0041 452/155 |
| 5,334,084 A | * | 8/1994 | O'Brien | A22B 5/20 452/157 |
| 7,918,718 B2 | | 4/2011 | Christensen et al. | |
| 9,513,234 B2 | | 12/2016 | Taniguchi et al. | |
| 9,546,968 B2 | | 1/2017 | Cooke | |
| 11,428,648 B2 | | 8/2022 | Ursella et al. | |
| 2005/0067570 A1 | * | 3/2005 | Retterath | A22C 17/0073 250/359.1 |

(Continued)

FOREIGN PATENT DOCUMENTS

| | | |
|---|---|---|
| EP | 3106863 A1 | 12/2016 |
| EP | 3813022 A1 | 4/2021 |

(Continued)

*Primary Examiner* — Richard T Price, Jr.
(74) *Attorney, Agent, or Firm* — Pearne & Gordon LLP; Michelle E. Tochtrop (57) ABSTRACT

An animal carcass is moved along a movement trajectory which passes through an inspection zone between at least one X-ray emitter and at least one X-ray detector, which are stationary relative to the inspection zone. X-ray detections are performed at successive moments during movement of the animal carcass through the inspection zone, the animal carcass being made to rotate around an axis of rotation which is transversal to lines of propagation of X-rays emitted by the at least one X-ray emitter in the inspection zone, so that what is obtained is a plurality of two-dimensional radiographic images of the animal carcass in different angular positions around the axis of rotation. The two-dimensional radiographic images are processed to determine a cutting pattern and/or a structure of the animal carcass, such as a position of bones, fat and/or lean parts in the animal carcass.

18 Claims, 3 Drawing Sheets

(56) References Cited

U.S. PATENT DOCUMENTS

| | | | |
|---|---|---|---|
| 2005/0257748 A1* | 11/2005 | Kriesel | A22B 5/007 |
| | | | 119/51.02 |
| 2008/0200107 A1 | 8/2008 | Christensen et al. | |
| 2014/0376693 A1 | 12/2014 | Taniguchi et al. | |
| 2015/0317803 A1 | 11/2015 | Cooke | |
| 2019/0142351 A1 | 5/2019 | Christensen et al. | |
| 2020/0375203 A1* | 12/2020 | Pfanstiel | G01B 11/2522 |
| 2021/0116395 A1 | 4/2021 | Ursella et al. | |
| 2021/0270756 A1 | 9/2021 | Ursella et al. | |
| 2022/0179299 A1 | 6/2022 | Glendenning | |

FOREIGN PATENT DOCUMENTS

| | | |
|---|---|---|
| EP | 3872482 A1 | 9/2021 |
| WO | 2006128456 A1 | 12/2006 |
| WO | 2008102148 A1 | 8/2008 |
| WO | 2015167585 A1 | 11/2015 |
| WO | 2017191163 A1 | 11/2017 |
| WO | 2020190153 A1 | 9/2020 |

* cited by examiner

METHOD AND PLANT FOR INSPECTING AN ANIMAL CARCASS

FIELD OF THE INVENTION

This invention relates in general to the meat food sector and specifically relates to a method for inspecting an animal carcass, in particular in order to determine a cutting pattern for it. The invention also relates to a plant for implementing the method.

DESCRIPTION OF RELATED ART

During the butchering process the carcass of the animal killed (for example a bovine, a pig or a horse) must be cut into smaller parts which are then packaged and offered for sale. The quality and commercial value of the individual parts depend not just on the region of carcass from which the part was obtained, but also on the presence of bones and the relative quantity of fat and lean parts.

In order to optimise cutting of the carcass it is useful to know how the carcass is structured, that is to say, where the bones are and how the fat and lean parts are distributed in it. It should be considered that, even for individuals of the same animal species, each carcass has its own characteristics which differentiate it from the others—although within a general pattern which is common to the individuals of the same species—and therefore optimisation of the cutting necessitates a knowledge of those own characteristics with appropriate precision.

For this reason, apparatuses have already been proposed for automatically determining the characteristics of an animal carcass, such as the apparatuses described in international patent applications WO 2006/128456 A1, WO 2015/167585 A1 and WO 2017/191163 A1.

The apparatuses described in those documents perform a scan of the animal carcass using a tomographic scanner similar to those for medical use in which the X-ray emitter and the respective receiver are mounted on opposite sides on a cylindrical frame rotatable relative to the subject to be scanned, which is positioned along the central axis of rotation of the cylindrical frame.

Indeed in those documents the animal carcass is positioned on a conveyor belt which translates horizontally and moves the animal carcass through the rotatable frame on which the X-ray emitter and the X-ray receiver are mounted, so that the emitter and the receiver rotate around the animal carcass.

One disadvantage of such apparatuses is that, as well as being mechanically complex and expensive, they are difficult to integrate into butchering plants in which the animal carcasses are moved while hanging on a movement line. Indeed the apparatuses described above require the carcass to be laid horizontally on the conveyor belt, rather than hanging vertically.

Another disadvantage of such apparatuses is that in at least some of the radiographic images obtained the X-rays have also passed through the conveyor belt, in addition to the animal carcass, and therefore it is necessary to apply correction algorithms to eliminate the attenuation produced by the conveyor belt. That involves processing complexity and affects the precision of the determination of the characteristics of the animal carcass.

In this context the technical purpose which forms the basis of this invention is to make a plant for inspecting—and if necessary cutting—an animal carcass, the plant overcoming the above-mentioned disadvantages or at least providing an alternative to the prior-art technical solutions. The technical purpose and the aims specified are substantially achieved by a method, as well as by a plant, according to this disclosure.

The term "animal carcass" means the body of an animal killed and if necessary which has already undergone skinning and evisceration. For the purposes of this disclosure, the term "animal carcass" may also mean only a part of the body of the animal, for example a side or a quarter. The animal is for example a bovine, a pig or a horse, but may be any other animal.

The subject of this invention can be applied in particular in an abattoir, to divide the animal carcass into smaller parts to be sent for further processing or offered for sale.

For this purpose, in one specific example of application the invention is usable to determine a cutting pattern for the animal carcass. The term "cutting pattern" means a map which identifies how the animal carcass must be cut into pieces, in particular identifying the position and the path of the cutting lines to be made using a suitable blade. In other words, the cutting pattern corresponds to instructions for cutting the animal carcass.

According to one aspect of this invention, the animal carcass to be inspected is made to rotate around an axis of rotation relative to an X-ray emitter and to the respective receiver, which in contrast are fixed.

Practically, unlike the prior art in which the X-ray emitter and the X-ray receiver rotate around the conveyor line and the animal carcass conveyed, in this invention in contrast the animal carcass rotates relative to the X-ray emitter and to the X-ray receiver.

That is useful because it allows X-ray scanning to be performed while the animal carcass is moved while hanging, therefore without substantially modifying the known movement systems in the sector. It is a technical solution which can also be integrated into existing plants without any particular technical difficulties. Moreover it is useful because, since there is no need to rotate a rotatable frame on which the X-ray emitter and the X-ray receiver are mounted, it is mechanically simpler and less expensive than the above-mentioned prior art solutions.

Finally, that technical solution is useful because during the scan the animal carcass can be supported (that is to say, mechanically held up) without its support being interposed between the X-ray emitter and the X-ray receiver, or in any case without the presence of the support creating interference in the radiographic images obtained.

Therefore, according to this invention, two-dimensional radiographic images of the animal carcass are acquired at successive moments during the step of moving the animal carcass through an X-ray inspection zone, at different angular positions of the animal carcass around its axis of rotation.

The two-dimensional radiographic images obtained are processed to determine a structure of the animal carcass (such as a position of bones, fat and/or lean parts); if required, the cutting pattern can be determined based on the structure determined.

Basically, the animal carcass is subjected to a computed tomography inspection in which the animal carcass rotates relative to a fixed radiographic apparatus; the structure is determined based on the results of the computed tomography, identifying or "segmenting" the various zones of interest (bones, fat, lean parts); the cutting process is optimisable based on this.

At least in one embodiment, during processing of the radiographic images the respective angular position of the animal carcass in the two-dimensional radiographic images obtained is also taken into account. For this purpose the angular position in each of the two-dimensional radiographic images is determined based on the radiographic images themselves, or is obtained from non-radiographic information acquired during the X-ray scan, such as optical images acquired by one or more cameras or readings by an encoder.

BRIEF DESCRIPTION OF THE DRAWINGS

Further features and the advantages of this invention will be more apparent in the detailed description below, with reference to a preferred, non-limiting embodiment of a plant for inspecting and cutting an animal carcass. Reference will be made to the accompanying drawings, in which.

DETAILED DESCRIPTION OF PREFERRED EMBODIMENTS OF THE INVENTION

With reference to the above-mentioned figures, a plant for inspecting and cutting an animal carcass is labelled with the reference number 1 and an animal carcass is labelled with the reference number 9. As already indicated, the plant 1 can be applied in particular in an abattoir and its function is to divide the animal carcass 9 into smaller parts or into pieces to be sent for further processing or offered for sale.

It should be noticed that what is shown in the figures is extremely schematic and is intended to allow an understanding of the invention. Therefore, it shall be understood that the illustration of the plant 1 and of its components in the figures is not a precise illustration of a real plant, which is much more complex than that shown. However, what is described here renders the making of a real plant accessible to the person skilled in the art in light of knowledge in the sector. The animal carcass 9 is also shown in an extremely simplified way in the figures as an irregular body with elongate shape.

The plant 1 comprises a movement line 11 for moving the animal carcass 9 along a movement trajectory 10. The movement line 11 is for example a conveyor chain which runs along guides above the animal carcass 9 and on which the animal carcass 9 can be hung.

According to one aspect of this invention, the movement line 11 is configured to constrain the animal carcass 9 in such a way that the animal carcass 9 is rotatable around an axis of rotation 90. Specifically, the axis of rotation 90 is transversal (for example, perpendicular) to the movement trajectory 10. More specifically, the axis of rotation 90 is substantially vertical and the movement trajectory 10—defined by the movement line 11—is a path (with straight stretches and/or curved stretches) which extends in a plane which is substantially horizontal or slightly inclined relative to a horizontal plane, at least in the section of interest for this invention. In one embodiment the movement line 11 is equipped with a hook 15 for hanging the animal carcass 9 on the movement line 11: the hook 15 is rotatable relative to the movement line 11 around said axis of rotation 90.

For example the hook 15 is hinged to the conveyor chain with a suitable mechanism, so that the hook 15 can rotate around the axis of rotation 90 which is transversal (in particular, perpendicular) to the conveyor chain and to its running line.

In other embodiments the animal carcass 9 may be constrained in a different way which still allows it to rotate, for example it could be suspended from the movement line 11 by means of a rope or could be rested and fixed in a vertical position on a rotatable support mounted on the movement line 11 (which in that case could be a conveyor belt below the animal carcass).

In general: before it is moved, the animal carcass 9 gets constrained to, in particular hung on, a support which is mounted on the movement line 11; the animal carcass 9 is constrained to the support in such a way that the animal carcass 9 is rotatable around the axis of rotation 90 or the support is rotatable around the axis of rotation 90 relative to the movement line 11 (as well as relative to the movement trajectory 10 defined by the latter).

Figure 1:
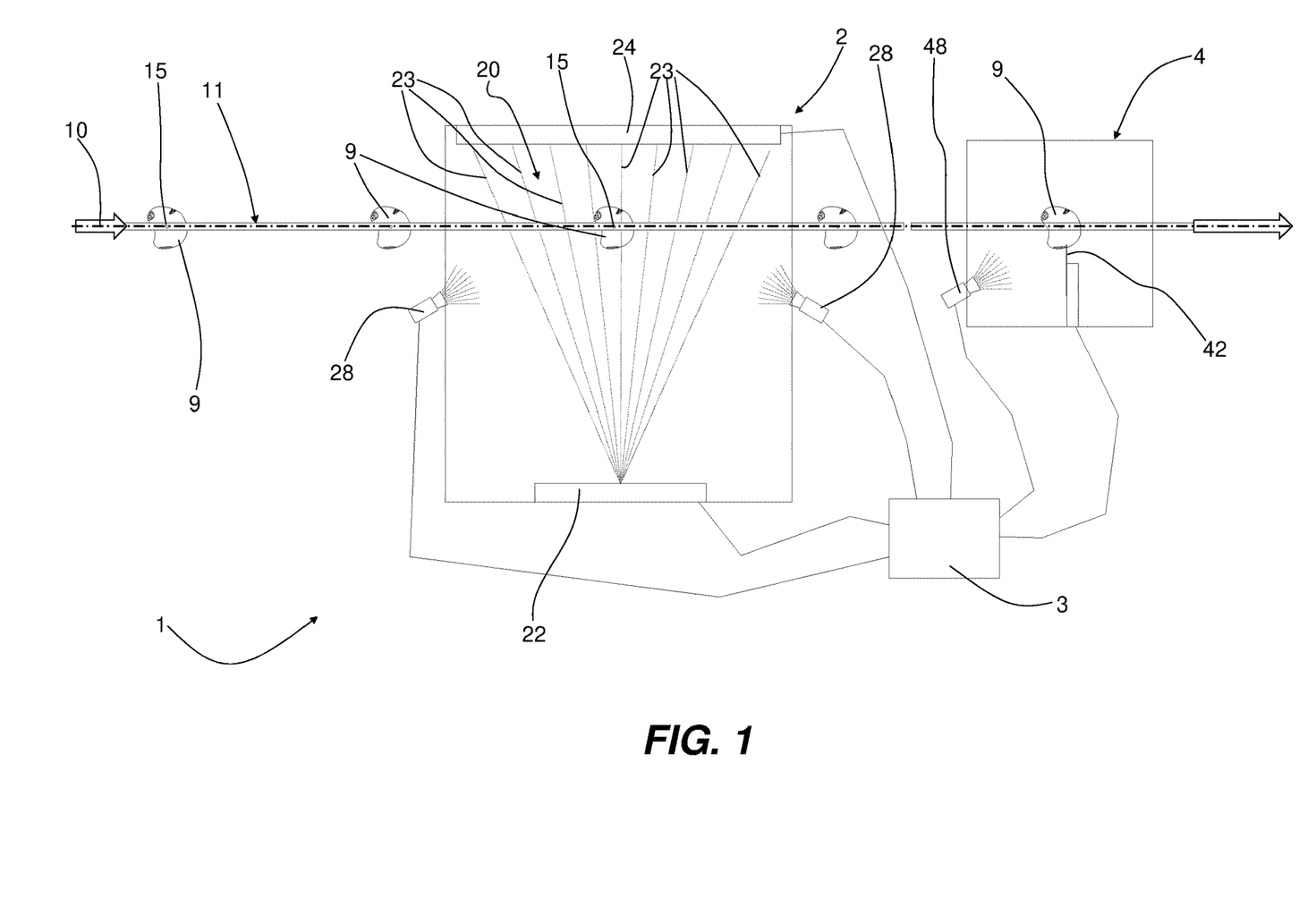
FIG. 1 schematically illustrates, in a top view, a plant for inspecting and cutting an animal carcass according to this invention.
Figure 2:
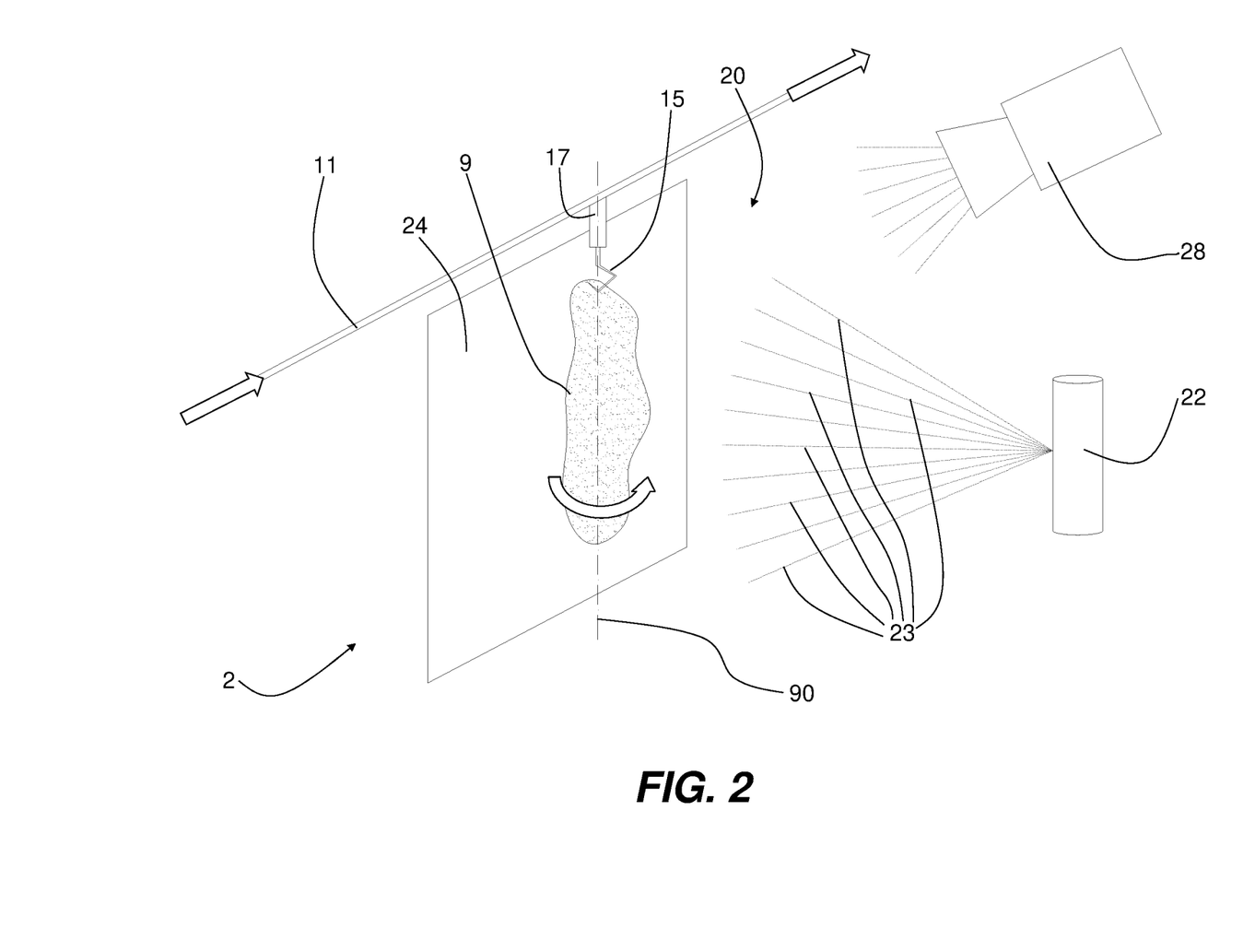
FIG. 2 schematically illustrates, in a perspective view, an X-ray inspection station which is part of the plant of FIG. 1.

Specifically and similarly to what is already known in the sector, the movement line 11 is configured to simultaneously move a plurality of animal carcasses 9—as shown in FIG. 1—therefore it is equipped with a respective plurality of hooks 15 (or of other supports for the animal carcasses) which are spaced apart along the movement trajectory 10.

The plant 1 also comprises an inspection station 2 through which the movement line 11 passes. The inspection station 2 has an inspection zone 20 in which the animal carcass 9, moved along the movement trajectory 10 through the inspection zone 20, is subjected to a radiographic inspection which specifically is a tomographic scan. In other words, the inspection zone 20 is an X-ray scan zone.

The inspection station 2 comprises at least one X-ray emitter 22 and at least one X-ray detector 24, between which the inspection zone 20 is located. As can be seen in the figures, the X-ray emitter 22 and the X-ray detector 24 are on opposite sides of the inspection zone 20 and on opposite sides of the movement line 11. The X-ray detector 24 is an X-ray receiver and corresponds to the X-ray receiver that is mentioned above in the general description of the invention.

The at least one X-ray emitter 22 and the at least one X-ray detector 24 are fixed relative to the inspection station 2, that is to say, they are stationary relative to the inspection zone 20 through which the animal carcass 9 passes.

The at least one X-ray detector 24 is facing the at least one X-ray emitter 22 to detect a residual intensity of the X-rays which passed through the animal carcass 9 moved through the inspection zone 20, that is to say, between the at least one X-ray emitter 22 and the at least one X-ray detector 24. The axis of rotation 90 of the animal carcass 9 is transversal to lines of propagation 23 of the X-rays in the inspection zone 20, that is to say, of the X-rays emitted by the emitter 22.

As is schematically shown in the figures, for example, the axis of rotation 90 is substantially vertical, whilst the emitter 22 emits a cone of X-rays which has a substantially horizontal central axis. Other spatial configurations, with axes along lines different from those indicated, are equally possible, provided that the axis of rotation 90 of the animal carcass 9 is transversal to lines of propagation 23 of the X-rays. For example, in other embodiments the animal carcass 9 may be shifted vertically or along the axis of rotation 90 during its rotation around the axis of rotation 90 in the inspection zone 20.

The plant 1 comprises a device for rotating the animal carcass 9 around the axis of rotation 90 as it passes through the inspection station 2, that is to say, as it passes through the inspection zone 20.

For example the rotation device is constituted of a motor 17 which is interposed between the conveyor chain and the hook 15 and which makes the hook 15 rotate around the axis of rotation 90 and consequently also makes the animal carcass 9 hanging on the hook 15 rotate.

Alternatively the rotation device may be constituted of a roller which rotates together with the hook 15 and of a fixed track which is parallel to the movement line 11 and with which the roller is in contact, so that during movement the roller rolls on the fixed track and causes the hook 15 and the hanging animal carcass 9 to rotate.

In yet another alternative the rotation device may act directly on the animal carcass 9 to impart to it a moment of force relative to the axis of rotation 90. For example the animal carcass 9 is suspended from the movement line 11 by means of a rope which, before entering the inspection station 2, is loaded by twisting in such a way that in the inspection station 2 the rope spontaneously unwinds thereby making the animal carcass 9 rotate.

Basically, movement of the animal carcass 9 through the inspection zone 20 comprises, in addition to translation of the animal carcass 9 along the movement trajectory 10 defined by the movement line 11, also a rotation of the animal carcass 9 around the axis of rotation 90, which is transversal to the lines of propagation 23 of the X-rays emitted by the at least one emitter 22. Moreover, in the specific embodiment illustrated, the axis of rotation 90 is transversal (in particular, is perpendicular) to the movement trajectory 10 in the inspection zone 20.

Therefore, as it passes through the inspection zone 20, the animal carcass 9 is in different linear positions (on the movement trajectory 10) and in different angular positions (relative to the axis of rotation 90). Therefore it performs a rotating—translating movement. The rotation and the translation are preferably simultaneous.

The at least one X-ray emitter 22 and the at least one X-ray detector 24 operate while the animal carcass 9 is moved through the inspection zone 20: a plurality of X-ray detections are performed by means of the at least one X-ray detector 24 at successive moments and a plurality of two-dimensional radiographic images is obtained of the animal carcass 9 in different positions relative to the at least one X-ray emitter 22 and to the at least one X-ray detector 24.

Since specifically said two-dimensional radiographic images are obtained with the animal carcass 9 in different angular positions around the axis of rotation 90—therefore in different angular positions relative to the emitter 22 and to the detector 24—they are radiographs of the animal carcass 9 from different viewpoints around the axis of rotation 90.

Figure 3:
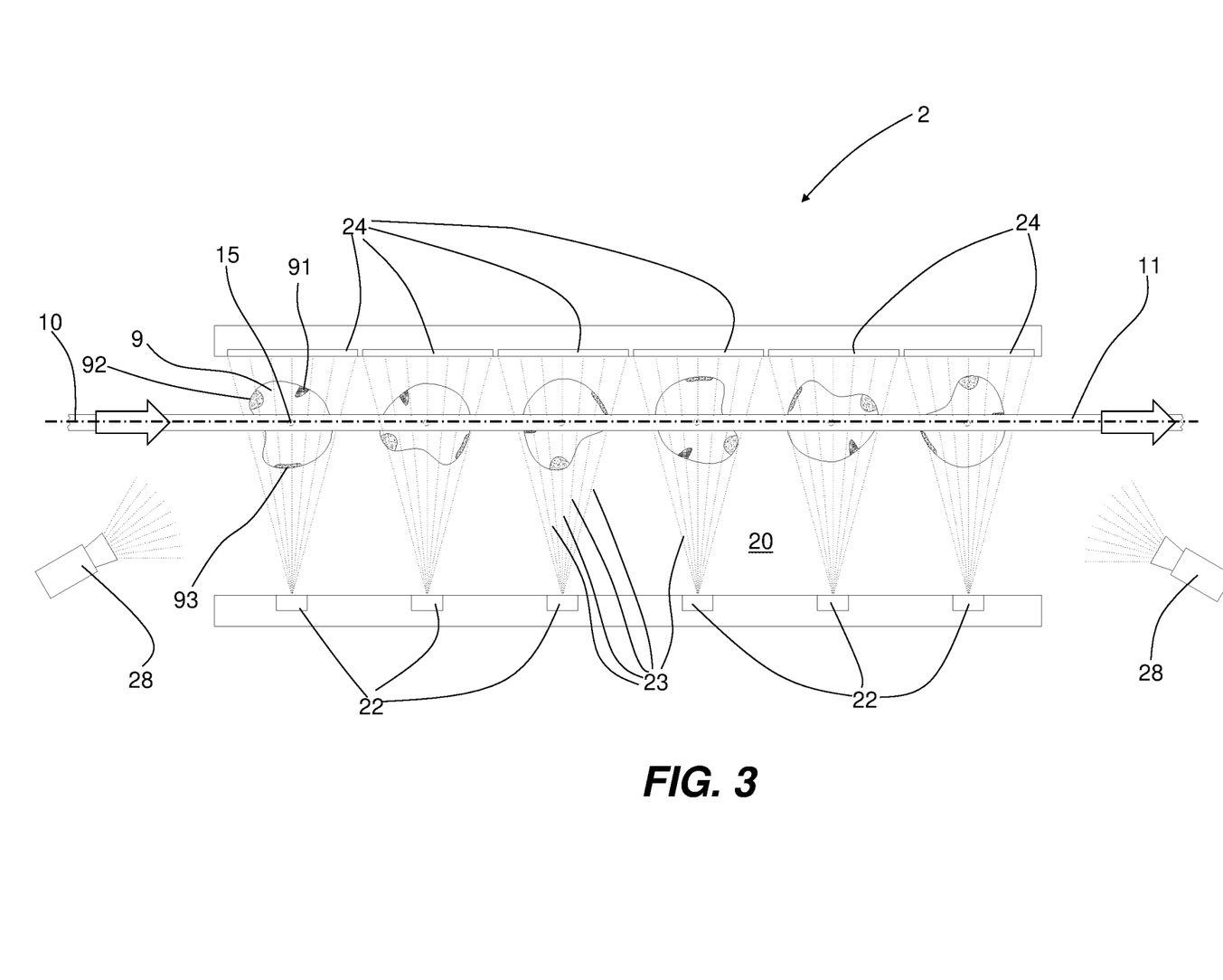
FIG. 3 schematically illustrates, in a top view, different positions of an animal carcass moved through an X-ray inspection station which is part of the plant of FIG. 1.

That is schematically shown in FIG. 3, where the same animal carcass 9 is illustrated in different positions along the movement trajectory 10 in the inspection station 2. The animal carcass 9 is rotated around the axis of rotation 90 between one position and another, therefore the respective radiographic images obtained are different views.

The speed of forward movement of the movement line 11, the angular speed of rotation of the animal carcass 9 around the axis of rotation 90 and the extent of the inspection zone 20 affected by the X-rays emitted by the at least one emitter 22 and detectable by the at least one detector 24 (essentially, the length of the stretch of movement trajectory struck by the X-rays) are selected in such a way that the plurality of two-dimensional radiographic images obtained is as representative as possible of the entire animal carcass 9, for example covering a complete rotation (or at least half a rotation or another angular amplitude sufficient to supply information suitable for a reliable tomography reconstruction) of the animal carcass 9 around the axis of rotation 90.

Roughly, the maximum speed of forward movement allowed is directly correlated with the extent of the inspection zone 20, whilst the minimum angular speed allowed is inversely correlated with the extent of the inspection zone 20.

To increase the extent of the inspection zone 20 affected by the X-rays it is possible to use a plurality of X-ray emitters 22, which are side by side parallel to the line of movement, and if necessary a plurality of X-ray detectors 24, which are side by side parallel to the line of movement. That is shown in a simplified way in FIG. 3. It should be noticed that, regarding this aspect, the solution described in European patent application EP 3872482 A1, for example, can be applied to the inspection station 2.

The use of a plurality of X-ray emitters 22 and if necessary of a plurality of X-ray detectors 24 may also be useful in the case of animal carcasses 9 which are very elongate along the axis of rotation 90; in this case the X-ray emitters 22 (and if necessary the X-ray detectors 24) are side by side along a line parallel to the axis of rotation 90.

The plant 1 comprises a computer 3 which is operatively connected to the inspection station 2. The computer 3 is configured to acquire, by means of the inspection station 2, the plurality of two-dimensional radiographic images of the animal carcass in different angular positions around the axis of rotation 90.

The computer 3 is also configured to process the plurality of two-dimensional radiographic images in order to determine a structure of the animal carcass 9, in particular a position of bones, fat and/or lean parts in the animal carcass 9, and/or in order to determine a cutting pattern for the animal carcass 9. The cutting pattern can be determined based on the structure determined, that is to say, the computer 3 develops a cutting pattern which is optimised for the specific animal carcass 9.

Practically, the computer 3 processes the radiographic images to obtain a tomography reconstruction of the animal carcass 9 itself, in which the components of interest (bones, fat, lean parts, etc.) can be identified and "segmented" (that is to say, distinguished from each other by identifying their respective borders). The algorithms usable for this purpose are already known in themselves in the medical sector and, in general, in the sector of computed tomography.

Specifically, the cutting pattern determined by the computer 3 derives from an optimisation which takes into account the quality and the economic value of the individual pieces obtainable: amongst all of the possible cutting patterns which are applicable to an animal carcass, what is selected is the cutting pattern best suited to the specific animal carcass 9 in light of its structure which was determined from the plurality of radiographic images.

Methods for determining a cutting pattern starting from the structure of the animal carcass may in themselves be considered known in the sector.

In the embodiment illustrated the plant 1 comprises a cutting station 4 through which the movement line 11 passes and which is downstream of the inspection station 2 along the movement trajectory 10. In the cutting station 4 the animal carcass 9 is cut according to the cutting pattern determined by the computer 3 by processing the plurality of two-dimensional radiographic images.

For example the cutting station 4 is an automated station which comprises at least one blade 42 for cutting the animal carcass 9 and a control system which is configured to operate the at least one blade 42 based on the cutting pattern determined for the specific animal carcass 9.

The control system of the cutting station 4 is managed by the computer 3 or is at least connected to the latter.

In the embodiment illustrated, the inspection station 2 comprises at least one camera 28 for acquiring optical images of the animal carcass 9 when the latter is in the inspection zone 20. In particular the inspection station 2 comprises two cameras 28.

By means of the at least one camera 28, optical images of the animal carcass 9 are acquired simultaneously with the plurality of X-ray detections (that is to say, during the step of performing the plurality of detections). During the processing of the two-dimensional radiographic images, the respective angular positions of the animal carcass 9 relative to the axis of rotation 90 are obtainable from the optical images obtained by the at least one camera 28.

For example, the animal carcass 9 may have—and usually has due to its nature—one or more zones 91-92-93 of a certain colour or with a certain "pattern" (that is to say, with a certain surface texture or pattern, such as patches or stripes), such that they render the zone 91-92-93 identifiable and recognisable in the optical images. The one or more zones 91-92-93 are a reference which, inspecting the sequence of optical images, makes it possible to establish the angular position of the animal carcass in a certain optical image and therefore in the two-dimensional radiographic image obtained at the same moment.

That allows each two-dimensional radiographic image to be associated with the respective angular position, so as to take it into account during the processing step and in particular for processing the tomography reconstruction of the animal carcass 9. Regarding this aspect, for example the solution described in European patent application EP 3813022 A1 could be applied. It should be noticed that the angular position of the animal carcass in each radiographic image could be determined with different methods, alternative to or in combination with the optical images.

For example, the respective angular position may be determined based on the plurality of two-dimensional radiographic images themselves by identifying in them a specific element—such as a particular bone—and examining where and how that specific element is present in the radiographic images.

Alternatively or in combination, the respective angular position may be obtained from non-radiographic information acquired during the step of performing the plurality of X-ray detections. The optical images acquired by the at least one camera 28 are an example of non-radiographic information that can be used; another example is information supplied by an encoder which detects the angular position of the hook 15 (or of another support for the animal carcass 9) relative to the movement line 11.

Even considering that, in one embodiment the movement line 11 is equipped with one or more encoders suitable for supplying the computer 3 with information for determining a position of the animal carcass 9 in the inspection zone 20. It should be noticed that the term "encoder" means an angular position and/or linear position transducer; it is a device known in itself to the person skilled in the art.

For example, the movement line 11 is equipped with an encoder for measuring the forward movement of the movement line 11 itself; the information obtained allows the position of the specific animal carcass 9 along the movement trajectory 10 in the inspection station 2 to be determined.

Each hook 15 of the movement line 11 may be equipped with a respective encoder which measures its angular position around the axis of rotation 90; the information obtained allows the angular position of the respective animal carcass 9 to be determined, if the latter is constrained to the hook 15 in such a way as to rotate together with the hook 15.

Basically, the inspection station 2 is a fixed tomographic scanner in which the object to be inspected is made to rotate between a (fixed) X-ray emitter and a (fixed) X-ray receiver.

In the embodiment illustrated, the cutting station 4 also comprises at least one camera 48 for acquiring optical images of the animal carcass 9 when the latter is in the cutting station 4, in particular during the step of cutting according to the cutting pattern determined.

The optical images acquired by the camera 48 are used, in a similar way to that described above relative to the camera 28 in the inspection station 2, to determine the angular position of the animal carcass 9 relative to the cutting pattern. In other words, the processing of the optical images of the camera 48 allows the control system of the cutting station 4 to know how the animal carcass 9 is oriented and therefore allows operation of the blade 42 in compliance with the cuts to be made according to the cutting pattern.

It should be noticed that in one variant the plant 1 does not comprise the cutting station 4, in practice it is a plant only for inspecting the animal carcass 9. Cutting of the animal carcass 9 may be performed subsequently in another plant, in which the inspection carried out in the plant 1 is also taken into account.

The invention also relates to a method for inspecting an animal carcass 9. The method, which in particular is implemented by a plant according to the invention, comprises:

a step of moving the animal carcass 9 along a movement trajectory 10 which passes through the inspection zone 20 between the at least one X-ray emitter 22 and the at least one X-ray detector 24; the at least one emitter 22 and the at least one detector 24 are stationary relative to the inspection zone 20; the at least one detector 24 is facing the at least one emitter 22 to detect a residual intensity of the X-rays which passed through the animal carcass 9 moved through the inspection zone 20; the movement step also comprises a step of rotating the animal carcass 9 around an axis of rotation 90 which is transversal to lines of propagation 23 of the X-rays which pass through the animal carcass 9 (that is to say, in the inspection zone 20);

a step of performing a plurality of X-ray detections by means of the at least one detector 24; the detections are performed at successive moments during the movement of the animal carcass 9 through the inspection zone 20; what is obtained is a plurality of two-dimensional radiographic images of the animal carcass 9 in different angular positions of the animal carcass 9 around the axis of rotation 90, relative to the at least one emitter 22 and to the at least one detector 24;

a step of processing the plurality of two-dimensional radiographic images to determine a structure of the animal carcass 9, in particular a position of bones, fat and/or lean parts in the animal carcass 9.

It should be noticed that specifically the rotation step is simultaneous with a step of translation of the animal carcass 9 along the movement trajectory 10, that is to say, during the movement step the animal carcass 9 is rotating—translating.

In particular ways of implementing, similarly to what is described above, the processing step also takes into account the respective angular positions of the animal carcass 9 in the radiographic images obtained. The respective angular position for each of the radiographic images is determined based on the plurality of radiographic images or is obtained from non-radiographic information acquired during the step of performing the plurality of X-ray detections. In one example, the non-radiographic information is optical images of the animal carcass acquired simultaneously with the plurality of X-ray detections; in another example the non-radiographic information is supplied by one or more encoders.

In one way of implementing, before the movement step the animal carcass 9 gets constrained to, in particular hung on, a support (in particular a hook 15) which is mounted on the movement line 11 for moving the animal carcass 9 along the movement trajectory 10. The animal carcass 9 is constrained to the support in such a way that the animal carcass 9 is rotatable around the axis of rotation 90 or the support is rotatable around the axis of rotation 90 relative to the movement line 11.

The result of the inspection, that is to say, the information obtained about the structure of the animal carcass 9, is usable to develop the cutting pattern or, more generally, to define the subsequent processing. For example, based on the result it is possible to decide whether to proceed with cutting or to sell the carcass whole.

The invention also includes a method for cutting an animal carcass 9, comprising a step of determining the structure of the animal carcass 9—according to the inspection method described above—a step of determining the cutting pattern based on the structure determined and a step of cutting the animal carcass according to the cutting pattern determined. In one particular way of implementing, during the cutting step optical images of the animal carcass are acquired to obtain the angular position of the animal carcass relative to the cutting pattern.

The invention described above may be modified and adapted in several ways without thereby departing from the scope of the inventive concept as defined in the appended claims.

All details may be substituted with other technically equivalent elements and the materials used, as well as the shapes and dimensions of the various components, may vary according to requirements.

The invention claimed is:

1. A method comprising:
   a step of moving an animal carcass along a movement trajectory which passes through an inspection zone between at least one X-ray emitter and at least one X-ray detector, the at least one X-ray emitter and the at least one X-ray detector being stationary relative to the inspection zone, the at least one X-ray detector facing the at least one X-ray emitter to detect a residual intensity of X-rays which passed through the animal carcass moved through the inspection zone;
   a step of performing a plurality of X-ray detections by at least one X-ray detector, said detections being performed at successive moments during the step of moving the animal carcass through the inspection zone, thus obtaining a plurality of two-dimensional radiographic images of the animal carcass in different positions relative to the at least one X-ray emitter and to the at least one X-ray detector;
   a step of processing the plurality of two-dimensional radiographic images to determine a structure of the animal carcass;
   wherein the step of moving the animal carcass through the inspection zone comprises a step of rotating the animal carcass around an axis of rotation which is transversal to lines of propagation of the X-rays which pass through the animal carcass, so that the two-dimensional radiographic images are obtained in different angular positions of the animal carcass around said axis of rotation, the method being for inspecting the animal carcass to determine the structure of the animal carcass.

2. The method according to claim 1, wherein the processing step also takes into account the respective angular positions of the animal carcass in the two-dimensional radiographic images, the respective angular position in each of the two-dimensional radiographic images being determined based on the plurality of two-dimensional radiographic images or being obtained from non-radiographic information acquired during the step of performing the plurality X-ray detections.

3. The method according to claim 2, wherein, during the step of performing the plurality of X-ray detections, optical images of the animal carcass are acquired simultaneously with the plurality of X-ray detections, so that during the processing step the respective angular position of the animal carcass can be obtained from the optical images.

4. The method according to claim 1, wherein before the moving step the animal carcass is constrained to, or hung on, a support which is mounted on a movement line for moving the animal carcass along the movement trajectory, the animal carcass being constrained to, or hung on, the support in such a way that it is rotatable around said axis of rotation or the support being rotatable around said axis of rotation relative to the movement line.

5. The method according to claim 1, wherein the axis of rotation is transversal or perpendicular to the movement trajectory in the inspection zone.

6. A method for cutting an animal carcass, comprising a step of determining a structure of the animal carcass by the method of claim 1, a step of determining a cutting pattern based on the structure determined, and a step of cutting the animal carcass according to the cutting pattern determined.

7. The method according to claim 6, wherein during the cutting step optical images of the animal carcass are acquired to obtain the angular position of the animal carcass relative to the cutting pattern.

8. The method according to claim 1, wherein the step of processing the plurality of two-dimensional radiographic images determines a position of bones, fat and/or lean parts in the animal carcass.

9. A plant comprising:
   a movement line for moving an animal carcass along a movement trajectory, the movement line being configured to constrain the animal carcass in such a way that the animal carcass is rotatable around an axis of rotation;
   an inspection station through which the movement line passes and which comprises at least one X-ray emitter and at least one X-ray detector, an inspection zone being between the at least one X-ray emitter and the at least one X-ray detector, the at least one X-ray detector facing the at least one X-ray emitter to detect a residual intensity of X-rays which passed through the animal carcass moved through the inspection zone, wherein the at least one X-ray emitter and the at least one X-ray detector are stationary relative to the inspection zone and the axis of rotation of the animal carcass is transversal to lines of propagation of the X-rays in the inspection zone;
   wherein the plant comprises a device for rotating the animal carcass around the axis of rotation during the movement through the inspection zone,
   wherein the plant is for inspecting the animal carcass and comprises a computer which is configured to acquire, by the inspection station, a plurality of two-dimensional radiographic images of the animal carcass in different angular positions around said axis of rotation and is configured to process said plurality of two-dimensional radiographic images in order to determine a structure of the animal carcass and/or in order to determine a cutting pattern for the animal carcass.

10. The plant according to claim 9, wherein the inspection station comprises at least one camera for acquiring optical images of the animal carcass in the inspection zone.

11. The plant according to claim 9, wherein the movement line is equipped with a hook for hanging the animal carcass on the movement line, the hook being rotatable relative to the movement line around said axis of rotation.

12. The plant according to claim 11, wherein the axis of rotation is transversal or perpendicular to the movement trajectory.

13. The plant according to claim 9, wherein the movement line is equipped with one or more encoders suitable for supplying information for determining a position of the animal carcass in the inspection zone.

14. The plant according to claim 9, wherein the plant is also for cutting the animal carcass and comprises a cutting station through which the movement line passes and which is downstream of the inspection station along the movement trajectory, so that in the cutting station the animal carcass is cut according to a cutting pattern determined by the computer by processing of said plurality of two-dimensional radiographic images.

15. The plant according to claim 14, wherein the cutting station comprises at least one camera for acquiring optical images of the animal carcass, the computer being configured to process the optical images in order to determine an angular position of the animal carcass in the cutting station.

16. The plant according to claim 15, wherein the inspection station comprises at least one camera for acquiring optical images of the animal carcass in the inspection zone and/or wherein the movement line is equipped with one or more encoders suitable for supplying information for determining a position of the animal carcass in the inspection zone.

17. The plant according to claim 9, configured to implement a method comprising:
a step of moving an animal carcass along a movement trajectory which passes through an inspection zone between at least one X-ray emitter and at least one X-ray detector, the at least one X-ray emitter and the at least one X-ray detector being stationary relative to the inspection zone, the at least one X-ray detector facing the at least one X-ray emitter to detect a residual intensity of X-rays which passed through the animal carcass moved through the inspection zone;
a step of performing a plurality of X-ray detections by at least one X-ray detector, said detections being performed at successive moments during the step of moving the animal carcass through the inspection zone, thus obtaining a plurality of two-dimensional radiographic images of the animal carcass in different positions relative to the at least one X-ray emitter and to the at least one X-ray detector;
a step of processing the plurality of two-dimensional radiographic images to determine a structure of the animal carcass;
wherein the step of moving the animal carcass through the inspection zone comprises a step of rotating the animal carcass around an axis of rotation which is transversal to lines of propagation of the X-rays which pass through the animal carcass, so that the two-dimensional radiographic images are obtained in different angular positions of the animal carcass around said axis of rotation,
the method being for inspecting the animal carcass to determine the structure of the animal carcass.

18. The plant according to claim 9, wherein the structure of the animal carcass is the position of bones, fat and/or lean parts in the animal carcass.

* * * * *